US006855158B2

(12) United States Patent
Stolpmann

(10) Patent No.: US 6,855,158 B2
(45) Date of Patent: Feb. 15, 2005

(54) THERMO-REGULATING PATIENT SUPPORT STRUCTURE

(75) Inventor: James R. Stolpmann, Lawrenceburg, IN (US)

(73) Assignee: Hill-Rom Services, Inc., Wilmington, DE (US)

(*) Notice: Subject to any disclaimer, the term of this patent is extended or adjusted under 35 U.S.C. 154(b) by 118 days.

(21) Appl. No.: 09/951,577

(22) Filed: Sep. 11, 2001

(65) Prior Publication Data

US 2003/0046762 A1 Mar. 13, 2003

(51) Int. Cl.$^7$ .................................................. A61F 7/00
(52) U.S. Cl. ........................ 607/108; 607/114; 5/421; 5/618
(58) Field of Search ...................... 607/96, 108–112, 607/104; 5/421, 618, 713, 715, 118; 219/486

(56) References Cited

U.S. PATENT DOCUMENTS

| | | |
|---|---|---|
| 371,938 A | 10/1887 | Hinsdill |
| 750,179 A | 1/1904 | Foglesong |
| 1,110,494 A | 9/1914 | Kellogg |
| 1,399,095 A | 12/1921 | Webb |
| 1,772,310 A | 8/1930 | Hart |
| 2,272,481 A | 2/1942 | Rinkes et al. |
| RE22,763 E | 6/1946 | Clark |
| 2,415,455 A | 2/1947 | Barnes et al. |
| 2,582,648 A | 1/1952 | Mowbray |
| 2,606,996 A | 8/1952 | Westerberg et al. |
| 2,792,827 A | 5/1957 | Gravin et al. |
| 2,832,336 A | 4/1958 | Davis et al. |
| 2,910,259 A | 10/1959 | Johnson |
| 3,094,983 A | 6/1963 | MacLeod |
| 3,186,404 A | 6/1965 | Gardner |
| 3,227,440 A | 1/1966 | Scott |
| 3,268,922 A | 8/1966 | Moxley |
| 3,451,071 A | 6/1969 | Whiteley |
| 3,492,988 A | 2/1970 | De Mare |
| 3,580,615 A | 5/1971 | Prosser |

(List continued on next page.)

FOREIGN PATENT DOCUMENTS

| | | |
|---|---|---|
| CH | 678 390 | 9/1991 |
| DE | 937 724 | 1/1956 |
| DE | 2 200 823 | 7/1973 |
| DE | 82 28 688.4 | 1/1983 |
| DE | 39 01 336 | 7/1989 |
| DE | 44 47 431 | 6/1996 |
| DE | 195 34 956 | 3/1997 |
| EP | 0 292 218 | 11/1988 |
| EP | 0 542 383 | 5/1993 |
| EP | 0 757 907 A1 | 2/1997 |
| EP | 0 821 928 A2 | 2/1998 |
| EP | 0993818 | 4/2000 |
| FR | 2 391 716 | 12/1978 |
| FR | 2 435 245 | 4/1980 |
| FR | 2 493 695 | 5/1982 |
| FR | 2 648 706 | 12/1990 |
| GB | 2221387 | 2/1990 |
| GB | 2244000 | 11/1991 |
| WO | WO 87/06209 | 10/1987 |
| WO | WO 97/12531 | 4/1997 |
| WO | WO 00/19946 | 4/2000 |

OTHER PUBLICATIONS

US 5,813,067, 9/1998, Stacy et al. (withdrawn)
Gorix Electro–conductive Textiles, http://www.gorix.com/gorix/GORIX.HTM (accessed Jun. 24, 1999).

(List continued on next page.)

Primary Examiner—Roy D. Gibson
(74) Attorney, Agent, or Firm—Bose McKinney & Evans LLP

(57) ABSTRACT

An apparatus for regulating a temperature of a body support structure including at least one bladder. A temperature modulator is coupled to the at least one bladder for varying the temperature of fluid within the bladder.

32 Claims, 10 Drawing Sheets

U.S. PATENT DOCUMENTS

| | | | |
|---|---|---|---|
| 3,785,374 A | 1/1974 | Lipson | |
| 3,789,853 A | 2/1974 | Reinhard | |
| 3,854,156 A | 12/1974 | Williams | |
| 3,869,594 A | 3/1975 | Shively | |
| 3,918,458 A | 11/1975 | Nethery | |
| 3,967,627 A | 7/1976 | Brown | |
| 3,993,053 A | 11/1976 | Grossan | |
| 4,013,069 A | 3/1977 | Hasty | |
| 4,029,087 A | 6/1977 | Dye et al. | |
| 4,066,072 A | 1/1978 | Cummins | |
| 4,127,906 A | 12/1978 | Zur | |
| 4,132,262 A | * 1/1979 | Wibell | 165/206 |
| 4,149,529 A | 4/1979 | Copeland et al. | |
| 4,156,425 A | 5/1979 | Arkans | |
| 4,168,063 A | 9/1979 | Rowland | |
| 4,198,961 A | 4/1980 | Arkans | |
| 4,207,633 A | 6/1980 | Smith et al. | |
| 4,207,875 A | 6/1980 | Arkans | |
| 4,207,876 A | 6/1980 | Annis | |
| 4,253,449 A | 3/1981 | Arkans et al. | |
| 4,280,485 A | 7/1981 | Arkans | |
| 4,281,647 A | 8/1981 | Antypas | |
| 4,287,620 A | 9/1981 | Zur | |
| 4,305,168 A | 12/1981 | Holter et al. | |
| 4,320,746 A | 3/1982 | Arkans et al. | |
| 4,331,133 A | 5/1982 | Arkans | |
| 4,335,726 A | 6/1982 | Kolstedt | |
| 4,338,944 A | 7/1982 | Arkans | |
| 4,370,975 A | 2/1983 | Wright | |
| 4,372,297 A | 2/1983 | Perlin | |
| 4,373,222 A | 2/1983 | Wolfe et al. | |
| 4,375,217 A | 3/1983 | Arkans | |
| 4,396,010 A | 8/1983 | Arkans | |
| 4,402,312 A | 9/1983 | Villari et al. | |
| 4,423,308 A | 12/1983 | Callaway et al. | |
| 4,476,867 A | 10/1984 | Parks | |
| 4,481,937 A | 11/1984 | Arkans | |
| 4,483,029 A | 11/1984 | Paul | |
| 4,494,775 A | 1/1985 | Nash et al. | |
| 4,555,130 A | 11/1985 | McClain | |
| 4,574,812 A | 3/1986 | Arkans | |
| 4,637,083 A | 1/1987 | Goodwin | |
| 4,638,519 A | 1/1987 | Hess | |
| 4,648,392 A | 3/1987 | Cartier et al. | |
| 4,747,409 A | 5/1988 | Silen | |
| 4,773,397 A | 9/1988 | Wright et al. | |
| 4,803,744 A | 2/1989 | Peck et al. | |
| 4,858,596 A | 8/1989 | Kolstedt et al. | |
| 4,879,777 A | 11/1989 | Goodwin | |
| 4,896,389 A | 1/1990 | Chamberland | |
| 4,900,065 A | 2/1990 | Houck | |
| 4,914,760 A | 4/1990 | Hargest et al. | |
| 4,926,951 A | 5/1990 | Carruth et al. | |
| 4,934,002 A | 6/1990 | Watanabe | |
| 4,938,208 A | 7/1990 | Dye | |
| 4,941,221 A | 7/1990 | Kanzler | |
| 4,945,924 A | 8/1990 | Poettgen | |
| 4,949,412 A | 8/1990 | Goode | |
| 4,974,692 A | 12/1990 | Carruth et al. | |
| 4,977,629 A | 12/1990 | Jones et al. | |
| 5,007,411 A | 4/1991 | Dye | |
| 5,022,110 A | * 6/1991 | Stroh | 5/710 |
| 5,029,352 A | 7/1991 | Hargest et al. | |
| 5,031,604 A | 7/1991 | Dye | |
| 5,033,136 A | 7/1991 | Elkins | |
| 5,034,006 A | 7/1991 | Hosoda et al. | |
| 5,051,673 A | 9/1991 | Goodwin | |
| 5,074,285 A | 12/1991 | Wright | |
| 5,103,519 A | 4/1992 | Hasty | |
| 5,111,544 A | 5/1992 | Greabe | |
| 5,117,812 A | 6/1992 | McWhorter | |
| 5,154,185 A | 10/1992 | Latimer et al. | |
| 5,169,384 A | 12/1992 | Bosniak et al. | |
| 5,181,288 A | 1/1993 | Heaton et al. | |
| 5,182,826 A | 2/1993 | Thomas et al. | |
| 5,184,612 A | 2/1993 | Augustine | |
| 5,186,163 A | 2/1993 | Dye | |
| 5,201,102 A | 4/1993 | McClure | |
| 5,251,347 A | 10/1993 | Hopper et al. | |
| 5,263,473 A | 11/1993 | McWhorter | |
| 5,267,364 A | 12/1993 | Volk | |
| 5,279,010 A | 1/1994 | Ferrand et al. | |
| 5,300,101 A | 4/1994 | Augustine et al. | |
| 5,300,102 A | 4/1994 | Augustine et al. | |
| 5,311,623 A | 5/1994 | Hendi | |
| 5,323,500 A | 6/1994 | Roe et al. | |
| 5,324,320 A | 6/1994 | Augustine et al. | |
| 5,325,551 A | 7/1994 | Tappel et al. | |
| 5,331,698 A | 7/1994 | Newkirk et al. | |
| 5,336,250 A | 8/1994 | Augustine | |
| 5,342,285 A | 8/1994 | Dye | |
| 5,350,417 A | 9/1994 | Augustine | |
| 5,369,807 A | 12/1994 | Cho et al. | |
| 5,370,674 A | 12/1994 | Farrell | |
| 5,373,595 A | 12/1994 | Johnson et al. | |
| 5,375,273 A | 12/1994 | Bodine, Jr. et al. | |
| 5,390,382 A | 2/1995 | Hannant et al. | |
| 5,390,383 A | 2/1995 | Carn | |
| 5,394,576 A | 3/1995 | Soltani et al. | |
| 5,394,577 A | 3/1995 | James et al. | |
| 5,402,542 A | 4/1995 | Viard | |
| 5,415,618 A | 5/1995 | Koch | |
| 5,444,878 A | 8/1995 | Kang | |
| 5,448,878 A | 9/1995 | Hansen et al. | |
| 5,449,379 A | 9/1995 | Hadtke | |
| 5,483,709 A | 1/1996 | Foster et al. | |
| 5,522,871 A | 6/1996 | Sternlicht | |
| 5,533,218 A | 7/1996 | Fahy | |
| 5,539,942 A | 7/1996 | Melou | |
| 5,542,136 A | 8/1996 | Tappel | |
| 5,556,169 A | 9/1996 | Parrish et al. | |
| 5,560,374 A | 10/1996 | Viard | |
| 5,586,346 A | 12/1996 | Stacy et al. | |
| 5,588,167 A | 12/1996 | Pahno et al. | |
| 5,594,963 A | 1/1997 | Berkowitz | |
| 5,606,785 A | 3/1997 | Shelberg et al. | |
| 5,609,619 A | 3/1997 | Pompei | |
| 5,611,096 A | 3/1997 | Bartlett et al. | |
| 5,623,736 A | 4/1997 | Soltani et al. | |
| 5,626,556 A | 5/1997 | Tobler et al. | |
| 5,630,238 A | 5/1997 | Weismiller et al. | |
| 5,640,727 A | 6/1997 | Kappel | |
| 5,647,079 A | 7/1997 | Hakamiun et al. | |
| 5,658,325 A | 8/1997 | Augustine | |
| 5,666,681 A | 9/1997 | Meyer et al. | |
| 5,669,094 A | 9/1997 | Swanson | |
| 5,675,848 A | 10/1997 | Kappel | |
| 5,683,438 A | 11/1997 | Grahn | |
| 5,683,441 A | 11/1997 | Dickerhoff et al. | |
| 5,702,536 A | 12/1997 | Carruth | |
| 5,745,937 A | 5/1998 | Weismiller et al. | |
| 5,754,998 A | 5/1998 | Selton | |
| 5,759,149 A | 6/1998 | Goldberg et al. | |
| 5,773,275 A | 6/1998 | Anderson et al. | |
| 5,781,949 A | 7/1998 | Weismiller et al. | |
| 5,785,715 A | 7/1998 | Schatz | |
| 5,785,716 A | 7/1998 | Bayron et al. | |
| 5,794,288 A | 8/1998 | Soltani et al. | |
| 5,795,312 A | 8/1998 | Dye | |
| 5,802,646 A | 9/1998 | Stolpmann et al. | |
| 5,815,865 A | 10/1998 | Washburn et al. | |

| | | |
|---|---|---|
| 5,865,474 A | 2/1999 | Takahaski |
| 5,871,526 A | 2/1999 | Gibbs et al. |
| 5,881,410 A | 3/1999 | Yamada |
| 5,904,172 A | 5/1999 | Gifft et al. |
| 5,913,774 A * | 6/1999 | Feddema ............... 5/618 |
| 5,913,886 A | 6/1999 | Soloman |
| 5,920,934 A | 7/1999 | Hannagan et al. |
| 5,948,303 A | 9/1999 | Larson |
| 5,957,830 A | 9/1999 | Skulic |
| 5,959,149 A | 9/1999 | Bernardi |
| 5,966,762 A | 10/1999 | Wu |
| 5,966,763 A | 10/1999 | Thomas et al. |
| 5,970,550 A | 10/1999 | Gazes |
| 5,974,605 A | 11/1999 | Dickerhoff et al. |
| 5,983,429 A * | 11/1999 | Stacy et al. ............... 5/713 |
| 6,010,528 A | 1/2000 | Augustine et al. |
| 6,033,432 A | 3/2000 | Augustine et al. |
| 6,036,722 A | 3/2000 | Augustine |
| 6,049,927 A | 4/2000 | Thomas et al. |
| 6,052,851 A | 4/2000 | Kohnle |
| 6,061,855 A | 5/2000 | Flick |
| 6,073,284 A | 6/2000 | Borders |
| 6,078,026 A | 6/2000 | West |
| 6,088,642 A * | 7/2000 | Finkelstein et al. ......... 701/49 |
| 6,112,348 A | 9/2000 | Dickerhoff |
| 6,115,860 A | 9/2000 | Vrzalik |
| 6,138,676 A | 10/2000 | Bruhn |
| 6,149,674 A | 11/2000 | Borders |
| 6,156,058 A | 12/2000 | Kappel et al. |
| 6,159,574 A | 12/2000 | Landvik et al. |
| 6,168,612 B1 | 1/2001 | Augustine et al. |
| 6,178,578 B1 | 1/2001 | Soltani et al. |
| 6,182,316 B1 | 2/2001 | Thomas et al. |
| 6,212,718 B1 | 4/2001 | Stolpmann et al. |
| 6,269,497 B1 * | 8/2001 | Renfro ............... 5/118 |
| 6,282,735 B1 | 9/2001 | Stolpmann et al. |
| 6,295,675 B1 | 10/2001 | Ellis et al. |
| 6,311,348 B1 | 11/2001 | Luff et al. |
| 6,517,510 B1 * | 2/2003 | Stewart et al. ............. 604/31 |
| 6,606,754 B1 * | 8/2003 | Flick ................... 5/421 |
| 6,730,115 B1 | 5/2004 | Heaton |
| 2001/0020303 A1 | 9/2001 | Endo et al. |

OTHER PUBLICATIONS

Heated Beds, http://www.gorix.com/gorix/BEDS.HTM (accessed Jun. 24, 1999).

Electro–conductive Textiles??, http://www.gorix.com/gorix/WHATARE.HTM (accessed Jun. 24, 1999).

* cited by examiner

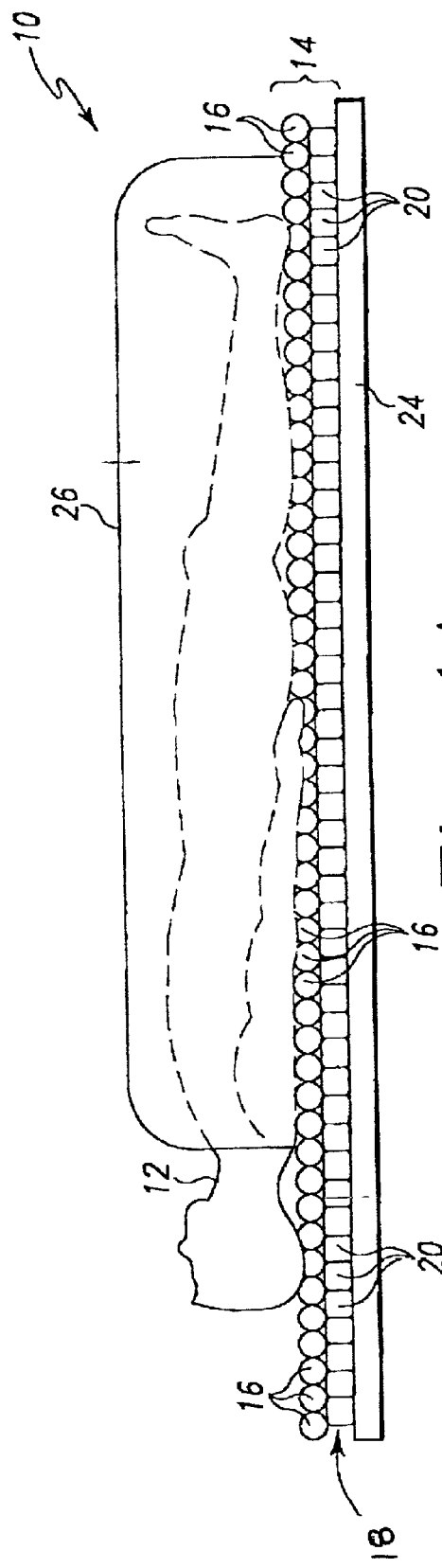
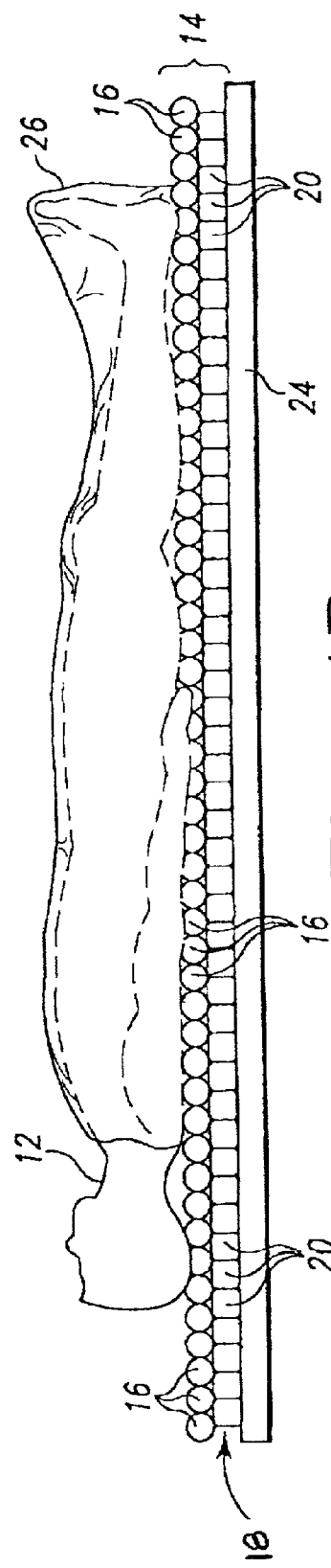

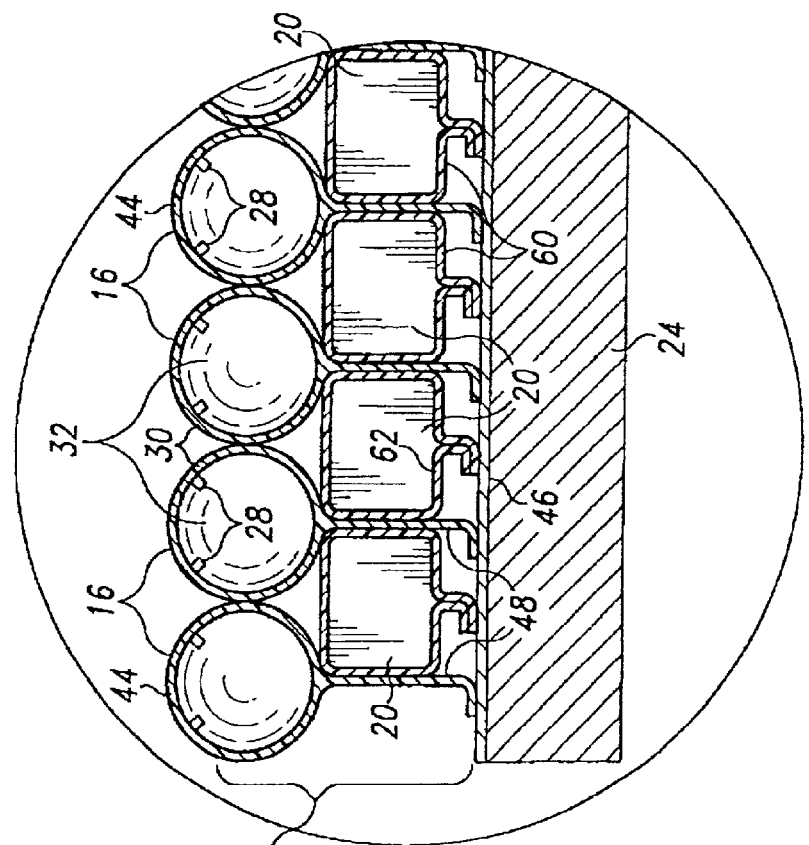
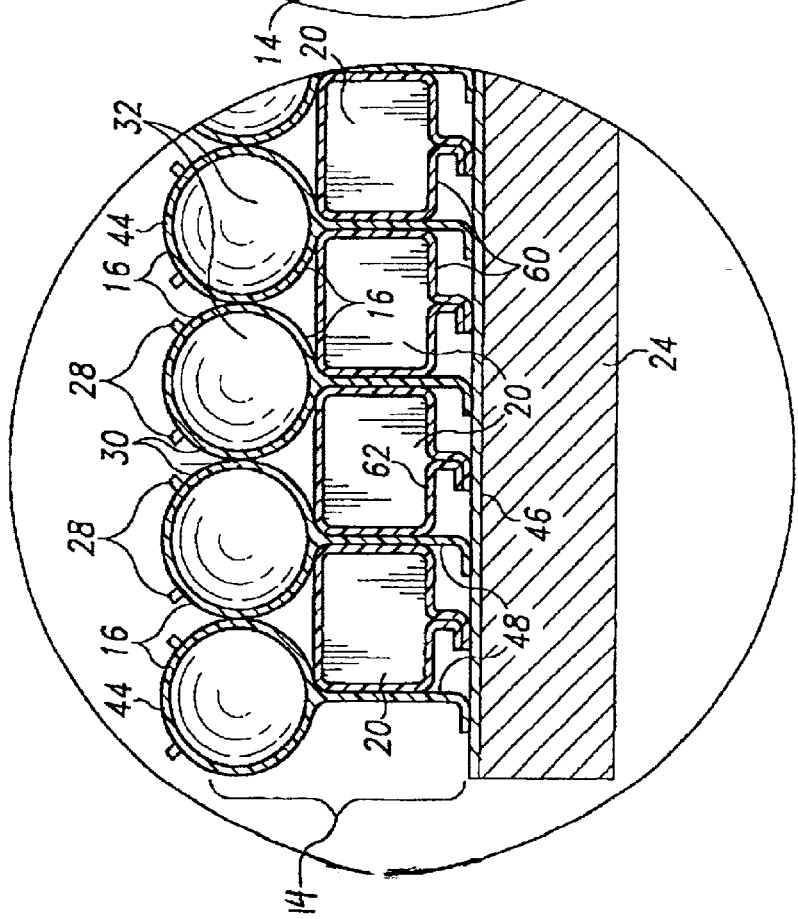
Fig. 2B
Fig. 2A

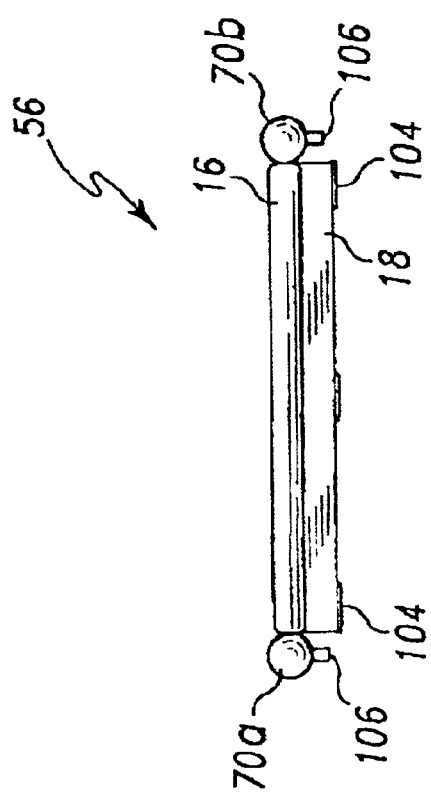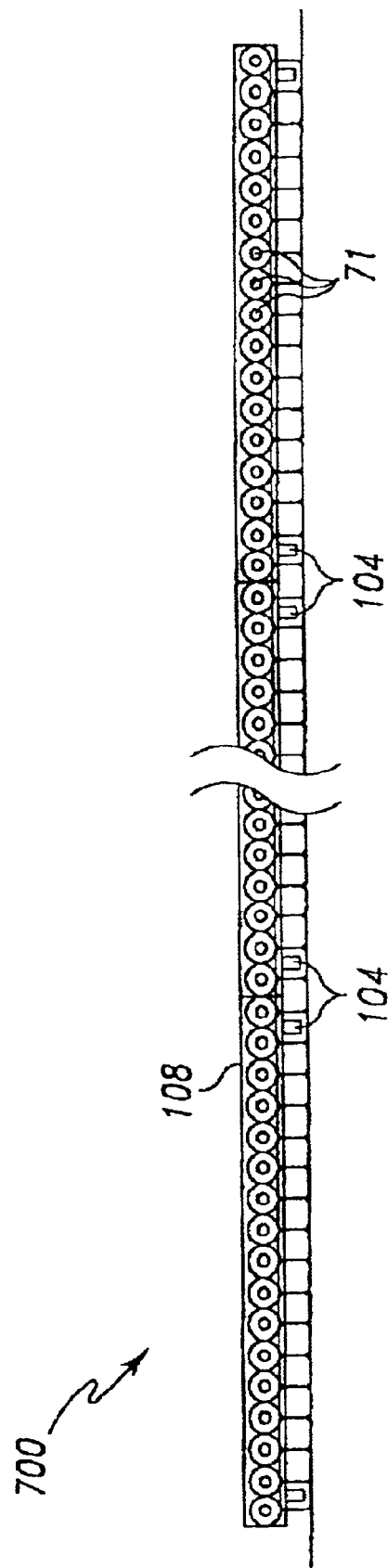

THERMO-REGULATING PATIENT SUPPORT STRUCTURE

BACKGROUND OF THE INVENTION

The present invention relates to an apparatus and method for regulating a body temperature of a person, such as a hospital patient. More particularly, the present invention relates to a mattress-style support structure having an inflatable layer for supporting a person and heating or cooling the person supported thereon.

Mattress pads capable of heating or cooling a patient are known in the art. Mattress pads capable of heating a patient typically include a conductive material which provides substantially uniform heat transfer across the pad. See, for example, U.S. Pat. No. 6,073,284 to Borders and U.S. Pat. No. 6,049,927 to Thomas, et al., both of which are assigned to the assignee of the present invention. U.S. Pat. No. 5,970,550 to Gazes discloses an inflatable mattress that may be filled with heated or cooled air or water using a heat pump or heat exchanger controlled by a thermostat. U.S. Pat. No. 6,033,432 to Augustine discloses an apparatus having a surface portion to which cooling is applied to remove heat from human or animal body portions in contact with the surface portion based upon the pressure applied by the body portion to the surface portion.

SUMMARY OF THE INVENTION

It is desirable to regulate the temperature of a mattress pad or other body support structure, including individual zones of the support structure, based on the present temperature thereof. It is also desirable to regulate the temperature of each of the individual zones independently of the other zones. Further, it is desirable to combine a temperature regulating apparatus and a pressure regulating apparatus in a single body support structure.

An apparatus according to an illustrative embodiment of the present invention is provided for regulating a temperature of a body support structure including an air bladder coupled to an air supply. The apparatus comprises a temperature sensor coupled to the air bladder to detect a temperature of the air bladder and to provide an output temperature signal indicative thereof. A temperature modulator is coupled to the air bladder and a controller is coupled to the temperature modulator and the temperature sensor to control the temperature of the air bladder based on the output temperature signal from the temperature sensor.

In illustrated embodiments, the body support structure includes a plurality of air bladders and a plurality of temperature sensors, at least one temperature sensor being coupled to each of the plurality of air bladders to detect the temperature of each of the plurality of air bladders separately and to provide an output temperature signal indicative of the temperature of the respective air bladder. The controller is coupled to the plurality of temperature sensors to control the temperature in each of the plurality of air bladders separately based on the output temperature signals received from the plurality of temperature sensors. In one illustrative embodiment, the temperature sensors are coupled to outer surfaces of the air bladders. In an alternative embodiment, the temperature sensors are located within an interior region of the air bladders.

Also according to an illustrative embodiment of the present invention, an apparatus is provided for controlling a temperature of a body support structure having a first bladder and a second bladder, each bladder coupled to a fluid supply. The apparatus comprises a temperature modulator coupled to the first and second bladders, and a controller coupled to the temperature modulator to control a temperature of the fluid in the first and second bladders independently.

In an illustrative embodiment, the temperature modulator includes first and second temperature modulators coupled to the first and second bladders, respectively. In a further illustrative embodiment, first and second temperature sensors are coupled to the first and second bladders, respectively, to detect first and second temperatures within the first and second bladders independently. The first and second temperature sensors are coupled to the controller to permit the controller to maintain temperatures within the first and second bladders at preselected temperatures.

Also according to an illustrative embodiment of the present invention, an apparatus is provided for regulating a temperature of a body support structure including a plurality of support zones, each support zone being coupled to a fluid supply. The apparatus includes a plurality of temperature modulators, each temperature modulator being coupled to one of the support zones. A controller is coupled to the plurality of temperature modulators to maintain the temperature in each of the plurality of support zones at an independent, preselected temperature. In a further illustrated embodiment, a plurality of temperature sensors are coupled between the fluid supply and the plurality of support zones to detect the temperature of the fluid supplied to the plurality of support zones.

According to a further embodiment of the present invention, a body support apparatus comprises a support structure configured to support a body, the support structure including a plurality of air bladders coupled to an air supply. A temperature control system is provided and includes a temperature modulator coupled to the plurality of air bladders and a controller configured to regulate the temperature of air supplied to the plurality of air bladders by the air supply. A reflective covering is positioned over the body. In an illustrative embodiment, the covering comprises a heat reflective material which is detachably coupled to the support structure. In a further illustrative embodiment, the covering comprises a permeable material.

According to yet another illustrative embodiment of the present invention, a support apparatus for a body comprises a mattress structure including a plurality of side-by-side base sections, a layer of material underlying the base sections, and a plurality of side-by-side air bladders overlying and being supported by the base sections. A plurality of tethers are provided, each tether connecting a respective one of the air bladders to the layer of material, and extending between a respective pair of the base sections. An air supply is coupled to the plurality of air bladders, and a temperature regulation system is coupled between the air supply and the plurality of air bladders. In a further illustrative embodiment, the temperature regulation system includes at least one temperature modulator coupled to the plurality of air bladders, and a controller coupled to the at least one temperature modulator to independently control the temperature of the air in each of the plurality of air bladders.

In yet another embodiment of the present invention, a system is provided for regulating the temperature and pressure of a body support structure, the support structure including a plurality of air bladder zones. The system comprises an air bladder inflation system including an air supply and a plurality of pressure sensors, each pressure sensor being configured to detect a pressure in an associated air bladder zone. A temperature regulation system includes a temperature modulator coupled to each of the plurality of air bladder zones and a plurality of temperature sensors, each temperature sensor being configured to detect a temperature of air in an associated air bladder zone. A controller is coupled to both the air bladder inflation system and the temperature regulation system to regulate both the pressure and the temperature of air in the plurality of air bladder zones. In illustrative embodiments, the controller regulates the pressure and temperature of air in each of the plurality of air bladder zones separately from the other air bladder zones.

According to still another embodiment of the present invention, an apparatus is provided for regulating a temperature of a body support structure, the apparatus comprising a low air loss air bladder having an upper support surface formed to include a plurality of holes. A temperature sensor is coupled to the air bladder to detect a temperature of the air bladder, and a blower is coupled to the air bladder. An air temperature modulator is coupled to the blower, and a controller is coupled to the temperature modulator and the temperature sensor to maintain a temperature of air provided to the air bladder at a preselected temperature based on an output from the temperature sensor. In an illustrative embodiment, the apparatus further comprises a blanket positioned above the body and the support structure to maintain the preselected temperature. In another illustrative embodiment, the air bladder has a lower support surface and an anti-skid pad coupled to a lower support surface.

Additional features and advantages of the present invention will become apparent to those skilled in the art upon consideration of the following description of the drawings exemplifying the best mode of carrying out the invention as presently perceived.

BRIEF DESCRIPTION OF THE DRAWINGS

FIG. 1A is a side elevational view of an embodiment of the present invention as used, in combination with a horizontal support member, to support and regulate the temperature of a human body;

FIG. 1B is a side elevational view of an alternative embodiment of the present invention as used, in combination with a horizontal support member, to support and regulate the temperature of a human body;

FIG. 2A is a cross-sectional view of an embodiment of the body support structure of the present invention;

FIG. 2B is a cross-sectional view of an alternative embodiment of the body support structure of the present invention;

FIG. 7 is an end view of the body support structure of FIG. 6;

FIG. 8 is a side elevational view, with a partial cut-away, of the body support structure of FIG. 6.

DETAILED DESCRIPTION OF THE DRAWINGS

Figure 3:
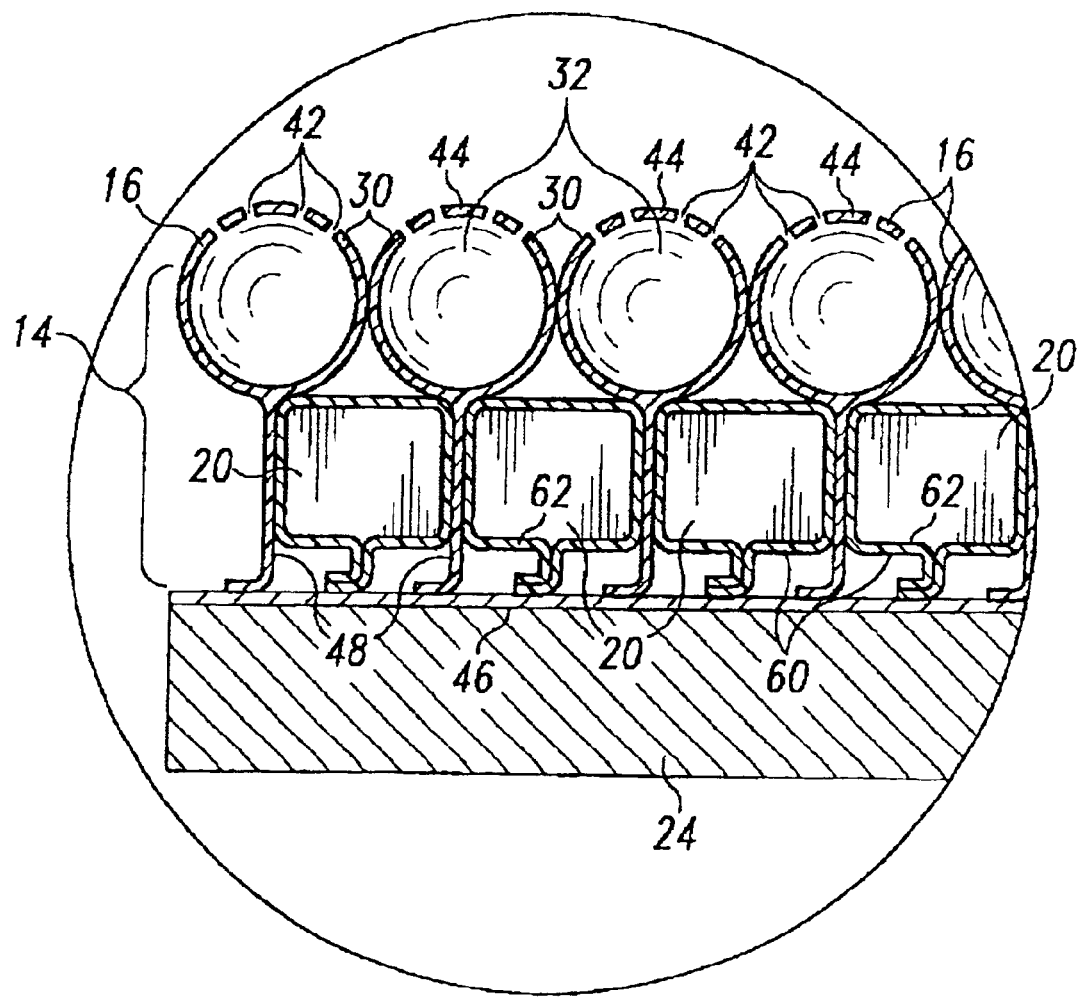
FIG. 3 is a cross-sectional view of a further embodiment of the body support structure of the present invention.

Referring initially to FIGS. 1A and 1B, apparatus 10 for regulating the temperature of a patient 12 in accordance with one embodiment of the present invention includes a mattress, or body support, structure 14. In the illustrated embodiments, support structure 14 includes a plurality of air bladders 16 supported by a base 18 having a plurality of separate base sections 20. For example, support structure 14 may comprise the air-over-foam mattress described in U.S. Pat. No. 6,212,718 to Stolpmann et al., which is assigned to the assignee of the present invention and which is expressly incorporated by reference herein. It should be appreciated that in other embodiments, support structure 14 may exclude base 18. Also, in other embodiments, an insulating layer (not shown) may be positioned between air bladders 16 and base 18. Further, in yet other embodiments, base 18 and/or air bladders 16 may be enclosed in an interior region defined by a cover of the type as disclosed in U.S. Pat. No. 6,212,718 to Stolpmann et al.

As shown in FIGS. 1A and 1B, support structure 14 is positioned on a horizontal support member 24, such as an operating room table or a deck of a bed. The horizontal support member 24 may comprise a conventional articulating deck (not shown) having pivotable head, seat, thigh, and leg sections. As the deck articulates, the body support structure 14 bends along with the respective deck sections.

A covering 26 is illustratively used to maintain the temperature of patient 12 at a desired level. As shown in FIG. 1A, covering 26 is coupled to support structure 14 to provide an enclosed region surrounding the patient 12. Alternatively, the covering 26 may be coupled to support member 24 to provide an enclosed region surrounding the patient 12. As illustrated in FIG. 1A, the covering 26 may inflate due to air escaping from the bladders 16 underneath the covering 26. In the embodiment of FIG. 1B, covering 26 comprises a shroud loosely positioned over the patient 12 without being coupled to either support structure 14 or support surface 24. In the illustrated embodiments, the covering 26 comprises a lightweight heat reflective material, such as Mylar. However, it is within the scope of the invention for the covering 26 to be comprised of other types of reflective or insulating material. Alternatively, the covering 26 may be formed of a breathable or permeable material which allows heated or cooled air to be vented away from the patient 12.

Referring now to FIGS. 2A and 2B, support structure 14 illustratively includes a plurality of temperature sensors 28 supported by the air bladders 16. The sensors 28 may be located either on an outer surface 30 of the air bladders 16 (FIG. 2A) or located in an interior region 32 of the air bladders 16 (FIG. 2B), respectively. Preferably, the temperature sensors 28 are supported by those portions of the air bladders 16 that are adjacent to the patient 12, and in particular, proximate the head and/or feet sections of the support member 24. Alternatively, temperature sensors 28 may be positioned in the vicinity of a circulator 34 (FIG. 4) or a fluid supply 36 (FIG. 5) in order to measure the temperature of air entering or exiting air bladders 16. Temperature sensors 28 are illustratively conventional temperature probes configured to measure the temperature of the air in their respective vicinity and to provide electrical output or temperature signals 38 indicative of the measured temperature to a controller 40 (FIGS. 4A and 4B). Temperature sensors 28 are illustratively coupled to the controller 40 through conventional means, including electrical wiring, cable or wireless transmission means.

As illustrated in the embodiments of FIGS. 2A and 2B, air bladders 16 may be of the "no air loss" type, meaning that air is generally retained with the interior region 32 of the bladders 16. Alternatively, air bladders 16 may be of the "low air loss" type, as illustrated in FIG. 3, meaning that each bladder 16 has a plurality of micro holes or vents 42 formed within an outer wall 44 through which the heated or cooled air is allowed to pass, or bleed, at a relatively slow rate from the interior region 32. Low air loss bladders 16 allow for the escape of the heated or cooled air into the area around the body 12 under covering 26. The air bladders 16 are illustratively comprised of a nylon twill or anti-friction shear material, or other similar material, having a low coefficient of friction which allows the bladders 16 to compress and uncompress with a minimal amount of friction therebetween.

Figure 6:
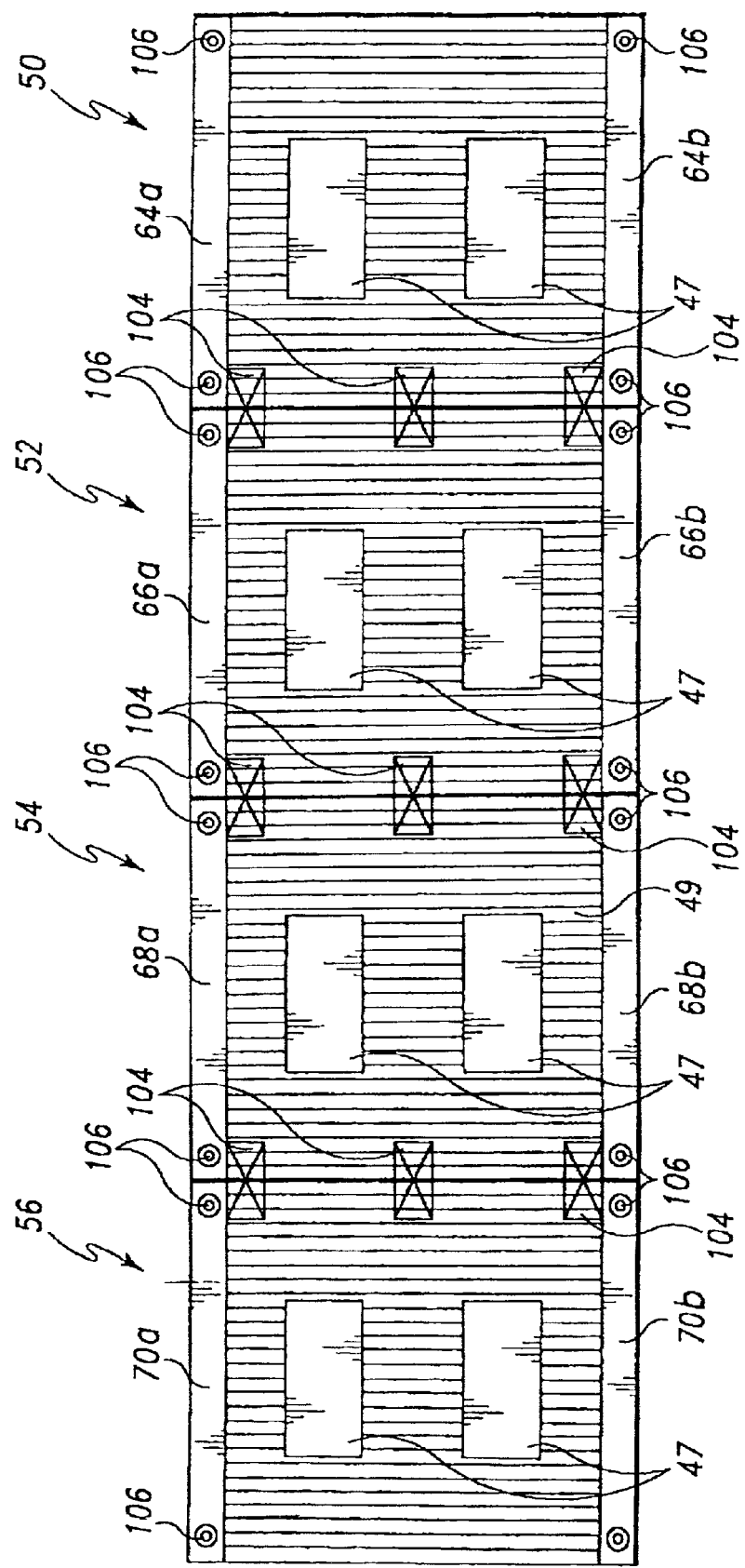
FIG. 6 is a bottom plan view of an embodiment of the body support structure of the present invention.

Referring further to the exemplary embodiments of FIGS. 2A, 2B, and 3, the air bladders 16 are coupled to a lower support material 46 via tethers 48, which extend between adjacent pairs of lower support elements or base sections 20. The tethers 48 are coupled to lower support material 46 using any conventional coupling means known in the art, such as RF welding, adhesive, snaps, buttons, or stitching. In illustrated embodiments, tethers 48 are formed integrally with transversely extending air bladders 16. However, it is within the scope of the invention for tethers 48 to be separate pieces that attach to air bladders 16 as well as lower support material 46. The lower support material 46 is positioned between base 18 and support member 24. Each tether 48 is illustratively made of an anti-friction shear material having a low coefficient of friction, such as nylon rip stop 30 denier or 1.5 mil polyurethane material. The lower support material 46 may include a plurality of anti-skid pads 47 coupled to a bottom surface 49 thereof to inhibit movement of the body support structure 14 relative to the support member 24 (FIG. 6).

The term "air" bladder is used in the description of the illustrated embodiments. However, it is within the scope of the present invention to use any one of many different types of fluids such as air, nitrogen, or water, to inflate a no-air-loss or low-air-loss bladder-type structure, as appropriate.

Hereinafter, the base sections 20 are referred to as form blocks 20. The plurality of foam blocks 20 are formed of omalized polyurethane foam or other material that is capable of withstanding heating and cooling. The firmness and support characteristics provided by each foam block 20 depend in part upon the indentation load deflection (ILD) of the foam from which each foam block 20 is made. The ILD is a well-known industry-accepted index indicating the "firmness" of material such as urethane foam and other foam rubber materials. A higher ILD rating indicates greater stiffness of the material. It is within the scope of the present invention for each foam block 20 to have substantially the same ILD ratings, or to provide at least one foam block 20 having a different ILD from the ILD of at least one other foam block 20.

Figure 4:
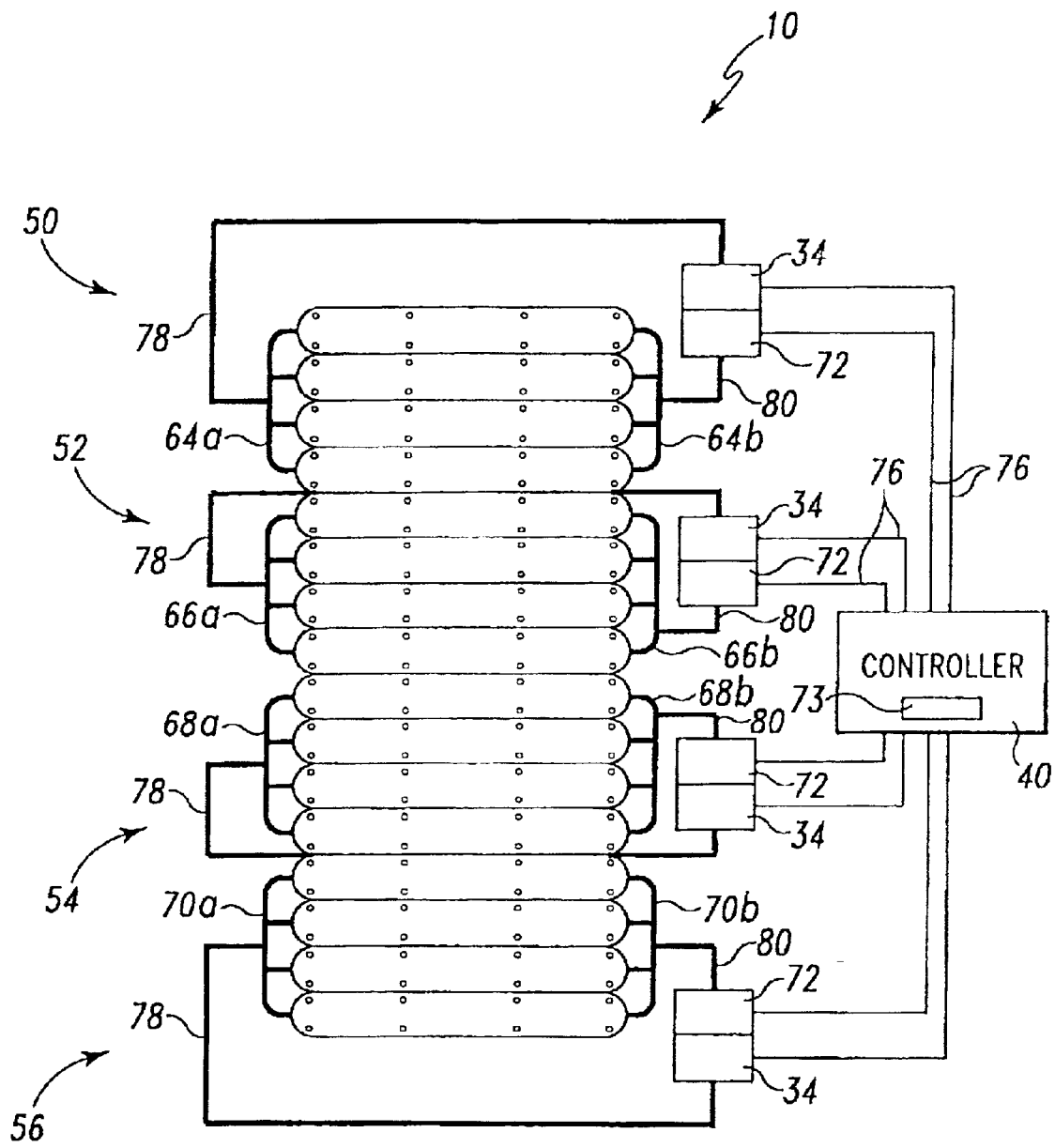
FIG. 4 is a diagrammatic view of an embodiment of the temperature regulating apparatus of the present invention.
Figure 4A:
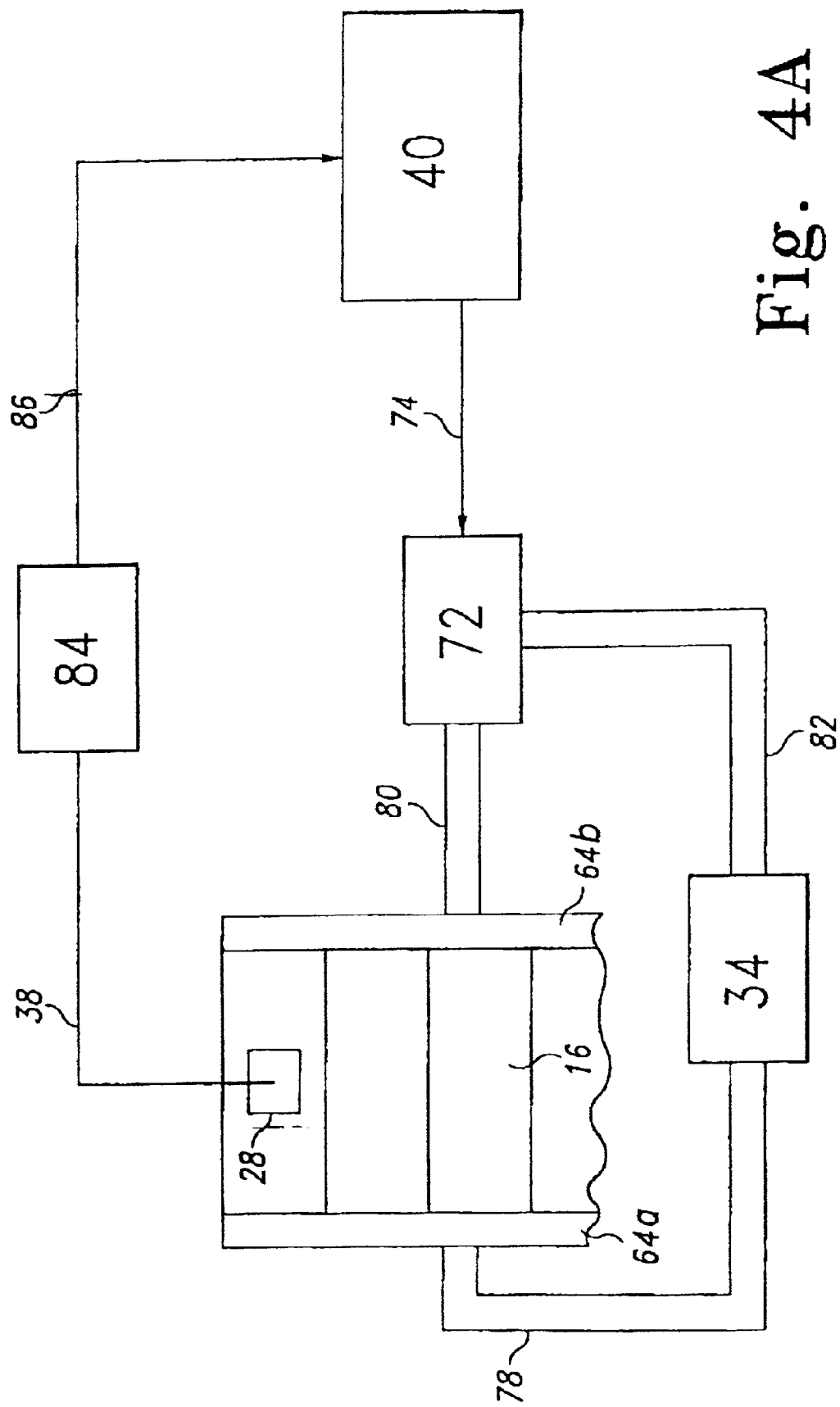
FIG. 4A is a diagrammatic view of an alternative embodiment of the temperature regulating apparatus of the present invention.
Figure 4B:
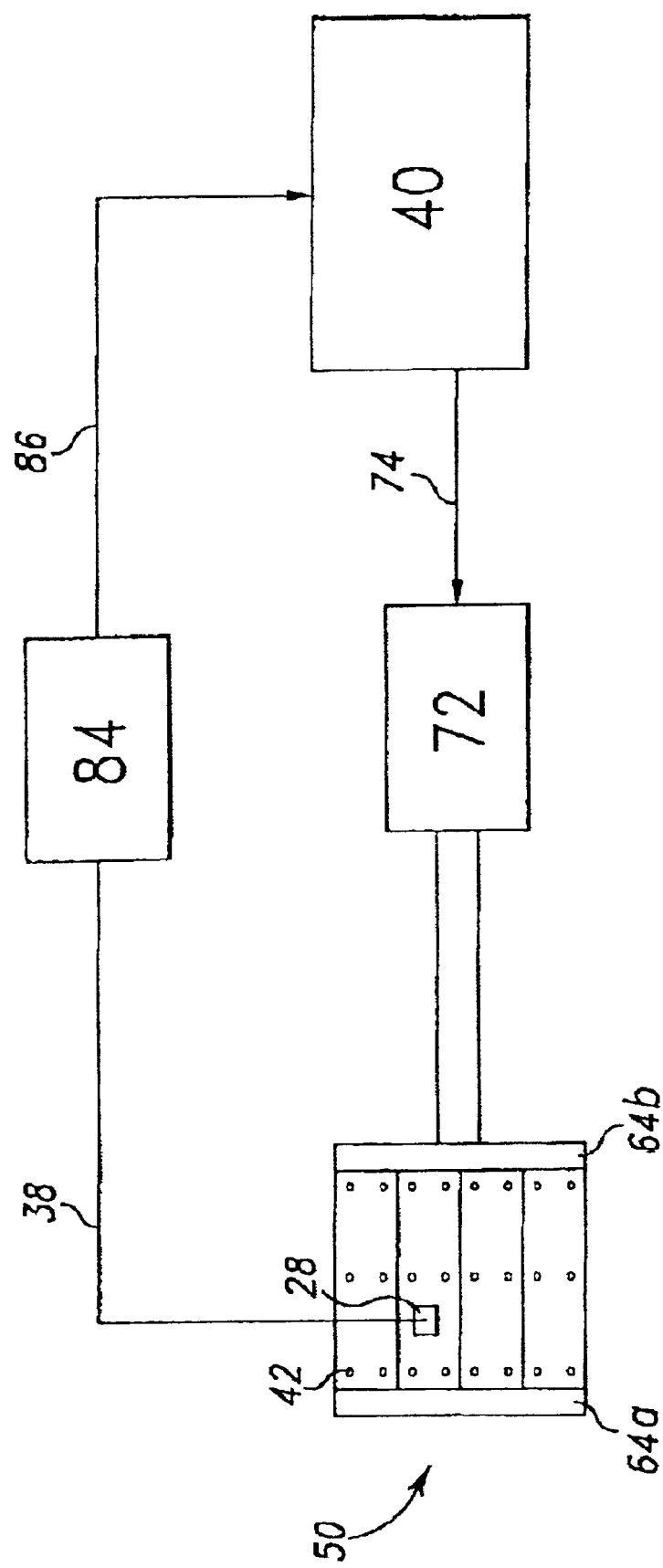
FIG. 4B is a diagrammatic view of a further embodiment of the temperature regulating apparatus of the present invention.

Referring to FIG. 4, the foam blocks 20 and associated bladders 16 provide the body support structure 14 with head, seat, thigh and foot zones 50, 52, 54, and 56, which are supported by respective underlying head, seat, thigh, and foot sections of the articulating deck or support member 24. The foam blocks 20 positioned in seat zone 52 preferably have a higher ILD rating than the foam blocks 20 positioned in head zone 50, foam blocks 20 positioned in thigh zone 54 preferably have the same ILD rating as foam blocks 20 positioned in head zone 50, and foam blocks 20 positioned in foot zone 56 preferably have a lower ILD than any of the foam blocks 20 positioned in head zone 50, seat zone 52, or thigh zone 54.

Referring again to FIGS. 2A, 2B and 3, the base 18 includes a plurality of square-shaped sleeves 60, each of which includes an interior region 62 and each of which is anchored to lower support material 46 by, for example, RF welding. Each sleeve 60 snugly receives at least one of the foam blocks 20. Engagement between the sleeves 60 and the foam blocks 20 cause the foam blocks 20 to resist transverse shifting within sleeves 60. In addition, securing sleeves 60 to the lower support material 46 prevents longitudinal shifting of foam blocks 20. Thus, sleeves 60 hold foam blocks 20 in their respective positions relative to lower support material 46. Moreover, securing foam blocks 20 and air bladders 16 to layer of support material 46 allows body support structure 14 to be moved as a single unit with foam blocks 20 and air bladders 16 remaining held in proper positions relative to one another and relative to layer of support material 46.

Figure 5:
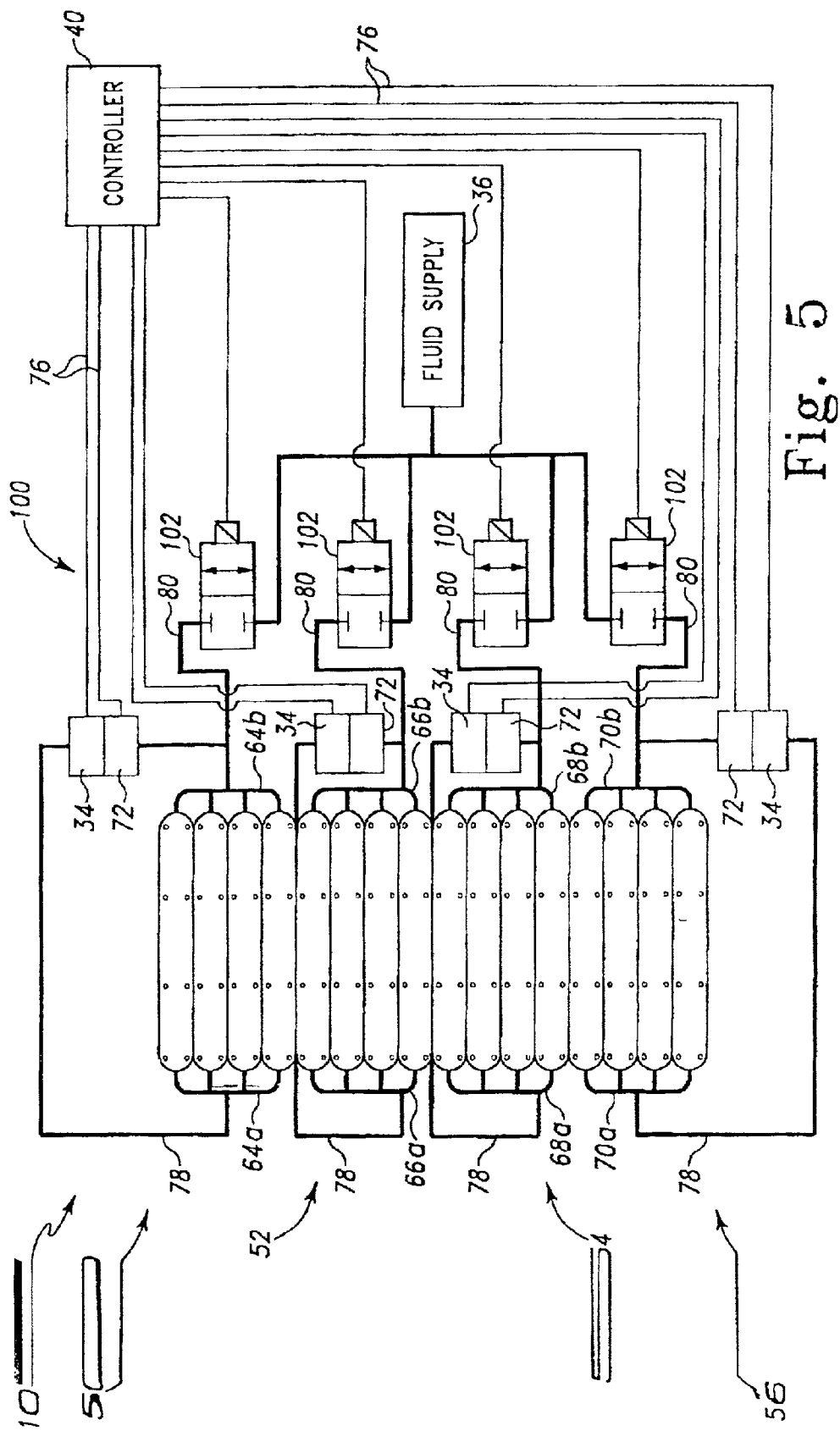
FIG. 5 is a diagrammatic view, similar to FIG. 4, of another embodiment of the temperature regulating apparatus of the present invention in combination with a pressure regulating system.

In the illustrated embodiments of FIGS. 4 and 5, the apparatus 10 includes a pair of head section manifolds or plenums 64a, 64b, a pair of seat section manifolds or plenums 66a, 66b, a pair of thigh section manifolds or plenums 68a, 68b, and a pair of foot section manifolds or plenums 70a, 70b. Manifolds 64, 66, 68 and 70 extend longitudinally relative to the body support structure 14. The air bladders 16 extend transversely between respective pairs of manifolds 64a, 64b, 66a, 66b, 68a, 68b, and 70a, 70b and are in fluid communication therewith. Manifolds 64, 66, 68, and 70 are generally made of the same low friction material as air bladders 16. A fluid port 71 (FIG. 8) is formed in each end of the air bladders 16 to provide fluid communication between the interior region of each bladder 16 and a respective manifold 64, 66, 68, 70.

Manifolds 64, 66, 68, and 70 and the transversely extending air bladders 16 associated therewith are sized so as to be supported by the respective sections of the articulating deck with which body support structure 14 is used. Thus, head section manifolds 64 and the associated transversely extending air bladders 16 are supported within the head zone 50 of body support structure 14. Similarly, seat, thigh, and foot section manifolds 66, 68, and 70 and the associated transversely extending air bladders 16 are supported within the seat, thigh, and foot zones 52, 54, and 56 of body support structure 14.

In the illustrated embodiment of FIG. 4, each support zone 50, 52, 54 and 56 includes four air bladders 16, each including a plurality of low-air-loss holes 42. The manifolds 64, 66, 68, and 70 are each coupled to a temperature modulator 72 and circulator 34. As such, the air bladders 16 in each support zone 50, 52, 54, and 56 are in fluid communication with a respective temperature modulator 72 and circulator 34, thereby defining an independent closed temperature control system for each support zone 50, 52, 54 and 56. The temperature of air in the air bladders 16 of each support zone 50, 52, 54, and 56 therefore may be independently regulated. The temperature modulator 72 and the circulator 34 for each support zone 50, 52, 54, and 56 is separately controlled by the controller 40 which is in communication therewith through conventional connector means, such as electrical wiring or cable 76.

Referring to FIGS. 4, 4A and 4B, controller 40 is configured to receive temperature signals 38, indicative of the measured temperature of the air within the bladders 16, from the sensors 28. The controller 40 compares the received temperature signals 38 to a preselected temperature value for each support zone. The preselected temperature value for each support zone 50, 52, 54, and 56 may be entered through a conventional input device, such as a keyboard (not shown) and stored within an internal memory 73 of the controller 40. The controller 40 may comprise a conventional programmable microprocessor for controlling the temperature modulator 72 and the circulator 34 via conventional connector means, such as electrical wiring or cable, based on the comparison of temperature signals 38 received from sensors 28 to the predetermined desired temperature for each support zone 50, 52, 54, and 56.

In response to the comparison, the controller 40 transmits a control signal 74 to each temperature modulator 72 instructing it to heat or cool the air in its respective support zone 50, 52, 54, 56. More particularly, the controller 40 determines, for a given point in time for each support zone 50, 52, 54, 56, a differential between the measured temperature indicated by the temperature signal 38 and the desired preselected temperature stored in memory 73. Should the differential be greater than a predetermined value, then the controller 40 instructs the temperature modulator 72 to cool the air supplied to the bladders 16 within the respective support zone 50, 52, 54, 56. Similarly, should the differential be less than a determined value, then the controller 40 instructs the temperature modulator 72 to heat air supplied to the bladders 16 within the respective support zone 50, 52, 54, 56.

FIG. 4 illustrates a closed system in which each temperature modulator 72 and circulator 34 is positioned intermediate respective manifolds 64a and 64b, 66a and 66b, 68a and 68b, and 70a and 70b in each support zone 50, 52, 54 and 56, respectively. More particularly, each first end manifold 64a, 66a, 68a, and 70a is coupled in fluid communication to a respective circulator 34 via air tight flexible tubing 78. Likewise, each second end manifold 64b, 66b, 68b, and 70b is coupled in fluid communication to a respective temperature modulator 72 using air tight flexible tubing 80. The circulator 34 and the temperature modulator 72 may also be coupled together in fluid communication using air tight flexible tubing 82 as illustrated in FIG. 4A.

The circulator 34 may comprise a conventional air circulator, such as a fan, blower, pump, compressor or other similar device for causing the movement of fluid. The circulator 34 may further comprise a conventional facility air system of the type providing air to patient rooms within a hospital. The temperature modulator 72 may comprise a conventional heat exchanger, thermoelectric cooling device, heat pump, heating or cooling element, or other similar device.

In the embodiments shown in FIGS. 4 and 4A, each circulator 34 draws air out of the respective support zone 50, 52, 54, 56 through the flexible tubing 78 and moves the air through or across the temperature modulator 72, which heats or cools the air in response to the control signals 74 received by the temperature modulator 72 from the controller 40. The heated or cooled air is then pushed through flexible tubing 80 and back into the respective support zone 50, 52, 54, 56. A similar closed-loop assembly is coupled to each support zone 50, 52, 54, and 56 of support structure 14. In other embodiments, temperature modulators 72 are associated with support zones 50, 52, 54, and 56 and are in direct thermal communication with respective air bladders 16 to heat or cool the air in the support zones 50, 52, 54, and 56 without the need for circulators 34.

As shown in FIGS. 4A and 4B, each temperature sensor 28 provides analog output temperature signals 38 to an analog-to-digital converter 84 via conventional wiring or cable, which transmits digital temperature signals 86 in digital form to controller 40, again via conventional wiring or cable. While only one sensor 28 is illustrated in the drawings, support structures 14 it is within the scope of the present invention to include a sufficient number of sensors 28 associated with each bladder 16 to ensure an accurate temperature reading. For illustrative purposes, the closed loop system associated with head zone 50 only is shown in FIGS. 4A and 4B. It should be appreciated that the seat zone 52, thigh zone 54, and foot zone 56 include substantially similar structures. While it is envisioned that only one temperature sensor 28 will be required for most applications, two spaced apart temperature sensors 28 may be utilized in order to calculate heat transfer. Moreover, a first temperature sensor 28 may be positioned proximate each respective inlet manifold 64a, 66a, 68a and 70a, and a second temperature sensor 28 may be positioned proximate each respective outlet manifold 64b, 66b, 68b and 70b. The difference between the temperatures ($\Delta$T) measured by the first and second temperature sensors 28 together with the mass flow and the specific heat of the fluid within the respective bladder 16 determines the amount of heat transfer. As such, the amount of heat supplied to or withdrawn from the patient may be calculated.

FIG. 4A shows in detail a support structure 14 having "no air loss" bladders 16. Although support structure 14 is shown as including four air bladders 16 in each support zone 50, 52, 54, and 56, this in no way limits the scope of the invention as each support zone 50, 52, 54, and 56 may include any number of air bladders 16.

FIG. 4B shows another embodiment of a support structure 14 having "low air loss" bladders 16 in support zones 50, 52, 54, and 56. Controller 40 transmits a control signal 74 to temperature modulator 72, and temperature modulator 72 provides heating or cooling to the air bladders 16 within head zone 50 via flexible tubing 80. In FIG. 4B, air escapes from holes 42 at a slow rate to circulate around the body of the patient 12. Sensors 28 and analog to digital converter 84 operate in a manner as described above.

FIG. 5 shows an embodiment of the temperature regulating apparatus 10 of the present invention in combination with an air pressure regulating system 100. Controller 40 includes software to control both the temperature and pressure of air within the air bladders 16 of each support zone 50, 52, 54, and 56. Fluid supply 36 is coupled to each support zone 50, 52, 54, and 56 via flexible tubing. Fluid supply 36 is, illustratively, a compressor, if no-air-loss bladders 16 are used, or, a blower, if low-air-loss bladders 16 are used. Coupled between each support zone 50, 52, 54, and 56 and fluid supply 36 is a pressure regulating valve 102. Each pressure regulating valve 102 is coupled to controller 40 so that the air pressure in each support zone 50, 52, 54, and 56 may be set independently. While it is within the scope of the present invention to combine the temperature regulating apparatus 10 with any suitable pressure regulating system 100 for air mattresses, in the illustrated embodiment, a pressure regulating system such as the one disclosed in U.S. Pat. No. 6,212,718 to Stolpmann et al., as expressly incorporated by reference herein, is used.

FIG. 6 is a bottom view of the support structure 14 illustrating head, seat, thigh and foot zones 50, 52, 54, and 56, each coupled together by fasteners 104. In the illustrated embodiment, three such fasteners 104 are used to couple each support zone 50, 52, 54, 56 to an adjacent support zone 50, 52, 54, 56. However, any number of fasteners 104 sufficient to keep the support zones 50, 52, 54, 56 from decoupling during use may be used. Fasteners 104 are illustratively textile material including hook and loop (Velcro) couplers, but could also include snaps, buttons, or could be sewn directly to the bottom surface of the support zones 50, 52, 54, 56 as detailed above. Base sections 20 extend transversely between respective manifolds 64a, 64b, 66a, 66b, 68a, 68b and 70a, 70b. Couplers 106 are used to couple manifolds 64, 66, 68, and 70 to flexible tubing 78 and 80 to enable air to circulate through the support zones 50, 52, 54, and 56. Each manifold 64, 66, 68 and 70 illustratively includes two couplers 106 in order to provide flexibility in connecting tubing thereto.

FIG. 7 is an end view of the body support structure 14 illustrating the foot zone 56, including base 18 with fasteners 104 coupled to the bottom surface thereof. The bladders 16 are positioned above base 18 and have substantially the same width as base 18. The manifolds 70a and 70b are positioned on opposite ends of support structure 14 and are separated by a distance substantially equal to the width of the bladders 16.

FIG. 8 is a side view, with a partial cut-away, of the body support structure 14 illustrated in FIG. 6, including head, seat, thigh and foot support zones 50, 52, 54, and 56. Each support zone 50, 52, 54 and 56 includes the base 18 comprised of plurality of base sections 20, a plurality of air bladders 16 positioned above the base 18 and having couplers coupling the air bladders 16 to manifolds 64, 66, 68 and 70 (FIG. 6). Cover 108 illustratively encloses the air bladders 140 for each support zone, but alternatively also encloses the base 160. Fasteners 104 are connected to sides of base sections 20.

Figure 9:
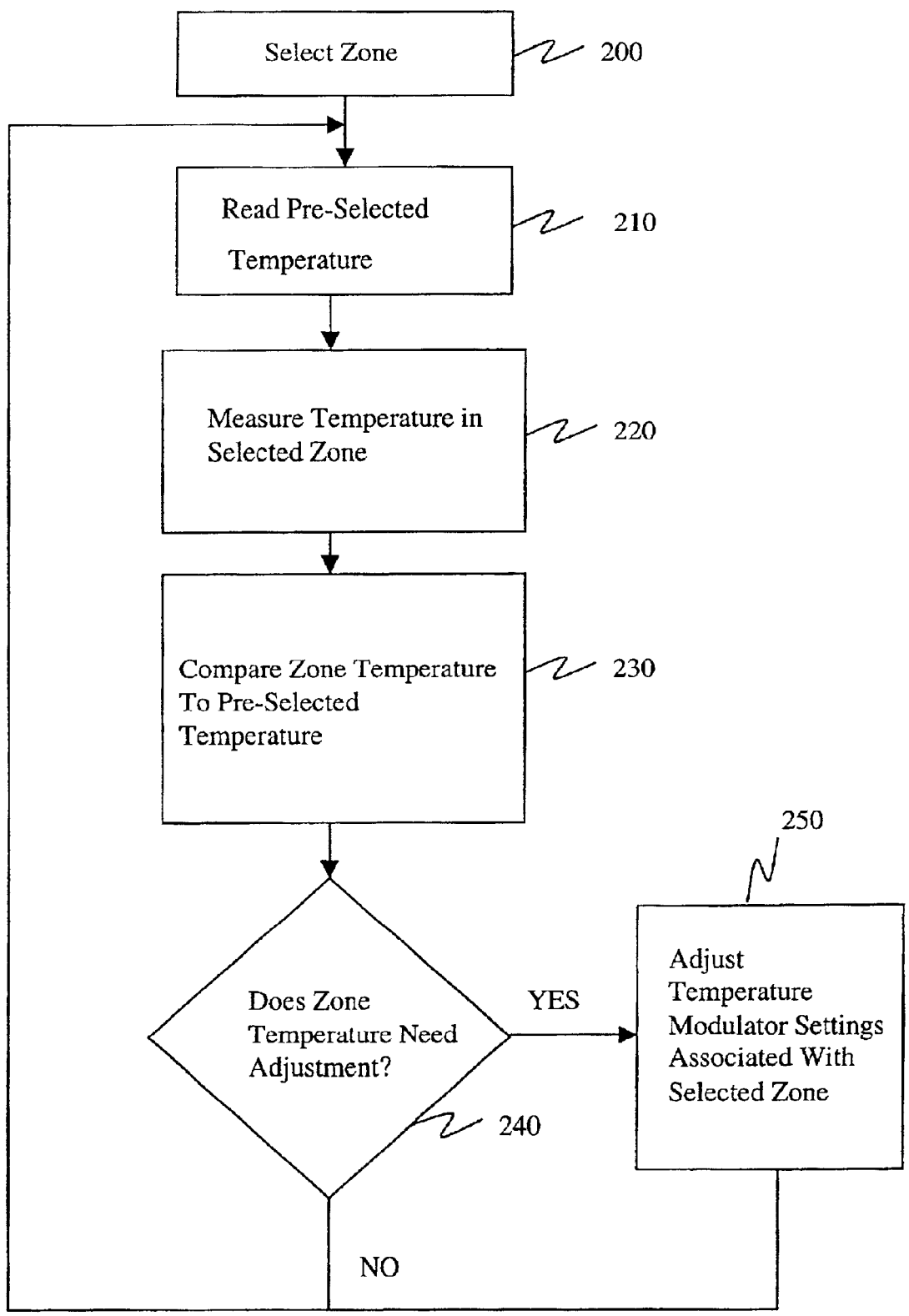
FIG. 9 is a flow chart of an embodiment of the temperature regulating process of the present invention.

FIG. 9 illustrates the process executed by controller 40 to regulate the temperature of support structure 14. At block 200, the support zone 50, 52, 54, 56 to be regulated is selected or detected from the measured temperature signal 38 received by the controller 40 from temperature sensors 28. At block 210, logic within controller 40 is used to determine the preselected desired temperature for the selected support zone 50, 52, 54, 56. As detailed above, the preselected temperature data (which may include a range or minimum and maximum permitted temperature) is electronically stored, such as in the computer database or digital file memory 73 that is accessible to controller 40 via a data access software utility, such as structured query language (SQL).

At block 220, the temperature reading is measured for the selected support zone 50, 52, 54, 56. If necessary, the temperature value is converted to the unit of measurement required by controller 40, such as from Celsius to Fahrenheit. An error tolerance range is also added to the temperature reading if necessary so that the temperature information reflects the degree of sensitivity of the temperature sensors 28.

At block 230, the measured temperature for the selected zone 50, 52, 54, 56 is compared to the preselected desired temperature for that zone, using programming logic executed by controller 40.

At block 240, logic is used by controller 40 to determine whether the temperature of the selected support zone 50, 52, 54, 56 needs to be adjusted by determining whether the difference between the preselected temperature and the measured temperature (if any) exceeds the acceptable range of tolerance levels.

If the temperature of the selected support zone 50, 52, 54, 56 needs to be adjusted, controller 40 uses logic to determine the amount of the needed adjustment and the appropriate instructions to transmit to the temperature modulator 72, at block 250. If the measured temperature is greater than the preselected temperature, controller 40 sends a signal to temperature modulator 72 to decrease the temperature in support zone 50, 52, 54, 56. If the measured temperature is less than the preselected temperature, controller 40 sends a signal to temperature modulator 72 to increase the temperature in support zone 50, 52, 54, 56. As described above, the temperature in the support zone 50, 52, 54, 56 is increased or decreased by the temperature modulator 72 which heats or cools the air supplied to the respective air bladders 16.

If the measured temperature is within the acceptable range of the preselected temperature, no temperature adjustment instructions are transmitted by controller 40 to temperature modulator 72. Temperature modulator 72 receives instructions from controller 40 in the form of electronic control signals 74, and adjusts the temperature in the selected support zone 50, 52, 54, 56 accordingly. Once the temperature adjustment is compete for one support zone 50, 52, 54, 56, or if no adjustment is necessary, the process illustrated by FIG. 9 is repeated for each support zone 50, 52, 54, 56. Alternatively, the process illustrated by FIG. 9 may occur concurrently for each support zone 50, 52, 54, 56.

Although specific embodiments of the invention have been disclosed, it will be understood by those of skill in the art that changes in form and details may be made without departing from the spirit and scope of the invention. The present invention is in no way limited to the specific embodiments illustrated herein. Accordingly, the present invention is to be defined and limited solely by the scope of the claims.

What is claimed is:

1. An apparatus for regulating a temperature of a body support structure comprising:

a plurality of air bladders defining a plurality of control zones, each of the plurality of air bladders having, an air inlet and an air outlet;

a plurality of temperature sensors, wherein at least one temperature sensor is coupled to each of the plurality of control zones to detect a temperature of air passing through the control zones and provide an output signal indicative thereof, a circulator coupled to the air bladders and configured to move air from the air outlets to the air inlets;

a temperature modulator coupled to the air bladders and configured to alter the temperature of air moved by the circulator, and a controller coupled to the circulator, the temperature modulator and the temperature sensors to control the temperature in each of the plurality of control zones based on the output signals from the temperature sensors.

2. The apparatus of claim 1, wherein the temperature modulator is coupled between the air outlet and the air inlet of the air bladders so that the temperature modulator controls the temperature of air supplied to the air bladders from the circulator.

3. The apparatus of claim 1, wherein the temperature modulator is a heat exchanger.

4. The apparatus of claim 1, wherein the temperature modulator is a heating element.

5. The apparatus of claim 1, wherein the temperature modulator is a cooling element.

6. The apparatus of claim 1, wherein the air circulator is a compressor.

7. The apparatus of claim 1, wherein the air circulator is a blower.

8. The apparatus of claim 1, wherein the air circulator is adapted to be connected to a facility air system.

9. The apparatus of claim 1, wherein the air bladders have an outer surface and the sensor is coupled to the outer surface of the air bladder.

10. The apparatus of claim 1, wherein the air bladders have an interior region and the sensors are located in the interior region of the air bladder.

11. The apparatus of claim 1, wherein the air bladders include a low air loss material.

12. An apparatus for regulating a temperature of a body support structure comprising:
   an air bladder having an air inlet and an air outlet;
   a temperature sensor coupled to the air bladder to detect a temperature of air passing through the air bladder and provide an output signal indicative thereof,
   a circulator coupled to the air bladder and configured to move air from the air outlet to the air inlet;
   a temperature modulator coupled to the air bladder and configured to alter the temperature of air moved by the circulator;
   a controller coupled to the circulator, the temperature modulator and the temperature sensor to control the temperature of the air bladder based on the output signal from the temperature sensor;
   a first manifold positioned longitudinally along a first side of the air bladder; and
   a second manifold positioned longitudinally along a second side of the air bladder, the first and second manifolds being coupled to the air bladder.

13. The apparatus of claim 12, wherein the first manifold and second manifold are positioned transverse to the air bladder.

14. An apparatus for regulating a temperature of a body support structure comprising:
   an air bladder having an air inlet and an air outlet;
   a temperature sensor coupled to the air bladder to detect a temperature of air passing through the air bladder and provide an output signal indicative thereof,
   a circulator coupled to the air bladder and configured to move air from the air outlet to the air inlet;
   a temperature modulator coupled to the air bladder and configured to alter the temperature of air moved by the circulator;
   a controller coupled to the circulator, the temperature modulator and the temperature sensor to control the temperature of the air bladder based on the output signal from the temperature sensor;
   a base positioned below the air bladder, and
   wherein the base includes a plurality of base sections, each having a different indention load deflection rating.

15. The apparatus of claim 14, wherein the base further includes a seat zone and a head zone, the seat zone having a higher indention load deflection rating than the head zone.

16. The apparatus of claim 14, wherein the base further includes a foot zone having a lower indention load deflection rating than the seat zone.

17. The apparatus of claim 14, wherein the base further includes a knee zone, the knee zone having the same indention load deflection ratings as the head zone.

18. An apparatus for regulating a temperature of a body support structure comprising:
   an air bladder having an air inlet and an air outlet;
   a temperature sensor coupled to the air bladder to detect a temperature of air passing through the air bladder and provide an output signal indicative thereof,
   a circulator coupled to the air bladder and configured to move air from the air outlet to the air inlet;
   a temperature modulator coupled to the air bladder and configured to alter the temperature of air moved by the circulator;
   a controller coupled to the circulator, the temperature modulator and the temperature sensor to control the temperature of the air bladder based on the output signal from the temperature sensor;
   a base positioned below the air bladder, and
   wherein the base includes a plurality of base sections, each comprising a polyurethane foam.

19. The apparatus of claim 18, wherein the polyurethane foam is omalized.

20. An apparatus for regulating a temperature of a body support structure comprising:
   an air bladder having an air inlet and an air outlet;
   a temperature sensor coupled to the air bladder to detect a temperature of air passing through the air bladder and provide an output signal indicative thereof,
   a circulator coupled to the air bladder and configured to move air from the air outlet to the air inlet;
   a temperature modulator coupled to the air bladder and configured to alter the temperature of air moved by the circulator;
   a controller coupled to the circulator, the temperature modulator and the temperature sensor to control the temperature of the air bladder based on the output signal from the temperature sensor; and
   a heat reflective covering adapted to be positioned over the body support structure.

21. The apparatus of claim 20, wherein the covering comprises air-permeable material.

22. An apparatus for controlling a temperature of a body support structure, the apparatus comprising:
   a first bladder coupled to a fluid supply;
   a second bladder coupled to a fluid supply;
   at least one temperature modulator coupled to the first and second bladders,
   the at least one temperature modulator including a heating element and a cooling element; and
   a controller coupled to the at least one temperature modulator to control a temperature of the fluid supply in the first and second bladders independently.

23. The apparatus of claim 22, wherein the at least one temperature modulator includes first and second temperature modulators coupled to the first and second bladders, respectively.

24. The apparatus of claim 22, further comprising first and second temperature sensors coupled to the first and second bladders, respectively, to detect first and second temperatures within the first and second bladders independently, the first and second temperature sensors being coupled to the controller to permit the controller to maintain temperatures within the first and second bladders at preselected temperatures.

25. An apparatus for regulating a temperature of a body support structure, the apparatus comprising:
   a plurality of support zones, each support zone being coupled to a fluid supply and configured to be inflated by the fluid supply for supporting a user;
   a plurality of temperature modulators, each temperature modulator being coupled to one of the support zones; and
   a controller coupled to the plurality of temperature modulators to maintain a temperature in each of the plurality of support zones at an independent, preselected temperature.

26. The apparatus of claim 25, further comprising a plurality of temperature sensors coupled between the fluid supply and the plurality of support zones to detect a temperature of the fluid supplied to the plurality of support zones.

27. An apparatus for regulating a temperature of a body support structure, the apparatus comprising:
   a plurality of support zones, each support zone being coupled to a fluid supply and configured to be inflated by the fluid supply for supporting a user;
   a plurality of temperature modulators, each temperature modulator being coupled to one of the support zones;
   a controller coupled to the plurality of temperature modulators to maintain a temperature in each of plurality of support zones at an independent, preselected temperature; and
   wherein the fluid supply is an air supply.

28. A system for regulating the temperature and pressure of a body support structure, the support structure including a plurality of air bladder zones, the system comprising:
   an air bladder inflation system including an air supply and a plurality of pressure sensors, each pressure sensor being configured to detect a pressure in an associated air bladder zone,
   a closed temperature regulation system including a temperature modulator coupled to each of the plurality of air bladder zones and a plurality of temperature sensors, each temperature sensor being configured to detect a temperature of air in an associated air bladder zone,
   each temperature modulator positioned intermediate an air outlet of the associated air bladder and an air inlet of the associated air bladder; and
   a controller coupled to both the air bladder inflation system and the temperature regulation system to regulate both the pressure and temperature of air in the plurality of air bladder zones.

29. The system of claim 28, wherein the controller regulates the pressure and temperature of air in each of the plurality of air bladder zones separately from the other air bladder zones.

30. An system for regulating a temperature of a body support structure, the system comprising:
   a low air loss air bladder having an air inlet, an air outlet, and an upper support surface formed to include a plurality of holes,
   a temperature sensor coupled to the air bladder to detect a temperature of air passing through the air bladder,
   a blower coupled to the air bladder and configured to move air from the air outlet to the air inlet,
   an air temperature modulator coupled to the blower and configured to alter the temperature of air moved by the blower, and
   a controller coupled to the temperature modulator and the temperature sensor to maintain a temperature of air provided to the air bladder at a preselected temperature based on an output from the temperature sensor.

31. The system of claim 30, further comprising a blanket positioned above the body and the support structure to maintain the preselected temperature.

32. The system of claim 30, wherein the air bladder has a lower support surface and an anti-skid pad coupled to the lower support surface.

* * * * *